United States Patent [19]
Wasserman et al.

[11] Patent Number: 5,171,148
[45] Date of Patent: Dec. 15, 1992

[54] DENTAL INSERTS FOR TREATMENT OF PERIODONTAL DISEASE

[75] Inventors: David Wasserman, Springfield; Shalaby W. Shalaby, Lebanon; Otis J. Bouwsma, East Brunswick, all of N.J.

[73] Assignee: Ethicon, Inc., Somerville, N.J.

[21] Appl. No.: 374,676

[22] Filed: Jun. 30, 1989

[51] Int. Cl.$^5$ .............................................. A61C 5/00
[52] U.S. Cl. .................................. 433/215; 424/426; 606/151/154
[58] Field of Search ......................... 433/136, 215, 229; 128/899; 606/151, 154, 155, 156; 424/426, 435, 444

[56] References Cited

U.S. PATENT DOCUMENTS

| | | | |
|---|---|---|---|
| 3,054,406 | 9/1962 | Usher | 606/151 |
| 4,428,375 | 1/1984 | Ellman | 606/151 |
| 4,531,916 | 7/1985 | Scantlebury et al. | 433/173 |
| 4,755,184 | 7/1988 | Silverberg | 623/16 |

FOREIGN PATENT DOCUMENTS 1249957 1/1989 Canada .
WO86/00517 1/1986 PCT Int'l Appl. .

OTHER PUBLICATIONS

Bertrand et al., "Activites de recherches sur un materiau biodegradeable en paradontologie: la polyglactine 910", Rev. Odontostomatol (Paris), vol. 14(2), pp. 113-123 (1985).

Quarta et al., "Repair of the Vestibule of the Mouth Using Polyglactin Netting", translated from German, Zahnarztl. Prax. vol. 36, pp. 344-352 (1985).

Holtje, W., "Wiederherstellung von Orbitabodendefekten mit Polyglactin", Fortschr. Kiefer Gesichtschir., vol. 28, pp. 65-67 (1983).

Brekke, et al., "Influence of polylactic acid mesh on the incidence of localized osteitis", Oral Surg., vol. 56, pp. 240-245 (1983).

Magnusson, et al. "New Attachment Formation Following Controlled Tissue Regeneration Using Biodegradable Membranes", J. Periodontol., vol. 59, pp. 1-6 (1988).

Fleisher, et al., "Regeneration of Lost Attachment Apparatus in the Dog Using Vicryl Absorbable Mesh (Polyglactin 910) ®" Inter. J. of Periodontics and Restorative Dentistry, pp. 45-56 (1988).

*Primary Examiner*—Cary E. O'Connor
*Attorney, Agent, or Firm*—Paul A. Coletti

[57] ABSTRACT

An absorbable mesh material useful as a dental implant. The mesh is cut by lasers to afford smooth edges which will not unravel. The implant may be attached by a ligature or suture material, generally formed from the same material as the implant, and attached to the implant by, among other things, laser or ultrasonic welding or interweaving.

8 Claims, 1 Drawing Sheet

DENTAL INSERTS FOR TREATMENT OF PERIODONTAL DISEASE

FIELD OF THE INVENTION

The present invention relates to methods and articles for treating periodontal disease. More specifically, the present invention relates to methods and articles to inhibit incursion of epithelium and to enhance healing of periodontal defects with the placement of absorbable inserts between the teeth and gingiva. Most specifically, the present invention relates to methods and articles for improving the inserts emplaced between teeth and gingiva for inhibiting incursion of epithelium and to enhance healing of periodontal defects.

BACKGROUND OF THE INVENTION

During the early stages of periodontal disease, known commonly as gingivitis, bacteria on the teeth and near the gingiva infect and irritate the sulcus where the gingiva approximates the tooth. The presence of bacteria can lead to destruction of the gingival epithelium which connects the gingiva to the tooth and can force the epithelium to separate from the root of the tooth. Also, as a result of bacterial presence, inflammatory cells increasingly populate the gingival tissues. Thus, the tissue is weaker due to the disease, and attachment is lessened. Of course, further infection moves the tissue attachment further toward the apex of the tooth, creating a pathological pocket much deeper than the normal sulcus.

Naturally, this pocket is difficult to clean or floss because the routine cleaning instruments of normal home care cannot reach the bacteria or plaque which accumulate within the pocket. As disease extends the pocket, the periodontal ligament which attaches the tooth to the supporting bone, and the supporting alveolar bone itself, are destroyed. This disease leaves a periodontal defect, filled with plaque and bacteria. Ultimately, the tooth could be surrounded by loose, diseased, and detached gingiva. Eventually such deterioration can result in the loss of the tooth.

One conventional treatment of periodontal defects consists of surgically gaining access to the root surface in an effort to remove bacteria and possible infected soft tissue and to alter the periodontal pocket or obtain reattachment of the connective tissue toward the crown of the tooth. Some of the former methods accomplish such attachment by cutting away gingival tissue near the crown of the tooth and if necessary shaping underlying bone to create a sulcus similar in depth to a normal sulcus so that regular oral hygiene may be used to maintain attachment of the gingiva to the tooth. Of course, such treatment does not recreate the attachment of the gingiva near the crown such as existed before any diseased condition. Such treatment also does not replace any periodontium lost to disease.

Another conventional treatment is known as a gingival flap procedure. One or more flaps of gingival tissue are retracted from the tooth. After the root is thoroughly cleaned, and diseased soft tissue is removed, these flaps are reopposed to the tooth. In some instances gingival grafts from other portions of the mouth are incorporated. Reattachment is unpredictable using this procedure. Gingival epithelium migrates rapidly along a tooth route toward the apex of the tooth, and bone cementum, and periodontal ligament migrate much more slowly. If the gingival epithelium is allowed to migrate toward the base of the periodontal defect, the gingival tissue is said to undergo a process called repair. The more desired process would allow the bone, cementum, and periodontal ligament cells to migrate coronally; this process is called regeneration. Repair is simply healing but regeneration is healing of the defect with the return of the defect towards the original condition.

Methods used to enhance the attachment of periodontal ligament to the tooth have usually tried to exclude gingival tissue from a healing defect site. For instance, the tooth surface has been etched with acids as some researchers have attempted to cause connective gingival tissue to attach to the tooth in order to stop the migration of the gingival epithelium toward the root. Other researchers have attempted to fill the defects with bone or artificial bone substitutes so that the bone portion of the defect may heal despite rapid growth of epithelium toward the root.

In other treatments, foils or other membranes into which gingival tissue cannot penetrate are used to separate the gingival tissue from the healing defect. In such a method, the epithelium migrates along one side of the membrane while the defect heals through ligament reattachment on the opposite side of the membrane.

These previous attempts to correct periodontal defects have not provided for attachment of periodontal ligament to the tooth while controlling the migration of the epithelium toward the root of the tooth. For this reason these techniques have met with quite limited success. In a most ideal case, periodontal disease should be treated by obtaining attachment of periodontal ligament to the tooth which will halt migration of the epithelium near the level maintained before the disease, and not more toward the apex of the tooth. In this case, the defect apical to the gingival attachment is healed by periodontal tissue which exists under the gingiva during the absence of periodontal disease.

One such method of causing such prevention of apical migration of gingival epithelium is to involve the placement of semipermeable or semiporous constructions between the tooth surface and the gingival tissue in an area in which periodontal disease has caused the attachment of the epithelium to the tooth to migrate toward the root of the tooth. Such a construction will not allow tissue to pass, but permits nutrients to pass between the tooth and gingiva. Upon placement of this construction against a portion of the perimeter of the tooth surface, the gingival tissue is positioned around the tooth, resulting in the construction being located between the gingival tissue and the tooth. During healing, the construction halts the apical growth of gingival epithelium so that periodontal ligament can healthily form, and is ready for attachment upon removal of the semiporous construction barrier.

These dental implants have taken on many forms. Some of the earlier forms of such dental implants were made from polytetrafluoroethylene (PTFE), a biocompatible but not bioabsorbable substance. Dental implants using PTFE gingival implant capably guarded against the apical migration of epithelium tissue while allowing the proper healing of periodontal ligament within the periodontal defect.

However, such dental implants have their own drawbacks. Specifically, a PTFE implant must necessarily be removed. Removal requires a subsequent surgical procedure which has proved inconvenient from the patient's standpoint, and, of course presented the possibility of infection or other complications as a consequence of the second surgical procedure.

Accordingly, other methods were followed using bioabsorbable polyester meshes. Studies undertaken in dogs included bone and muco-gingival surgery. Bony defects were isolated with such bioabsorbable meshes, which use exhibited no inflammatory reaction. Tissue regeneration was characterized in the appearance of periodontal ligament before the bioabsorption of the polyester mesh. Upon mesh absorption, tissue regeneration is effected and attachment of the periodontal ligament between the tooth and the alveolar bone is enhanced. The epithelial tissue does not migrate apically, and periodontal defects are resolved along with the normal formation of epithelium and periodontal ligament.

Other methods use such bioabsorbable polyester mesh implants with ligature material in order to accurately position the mesh around the tooth. Healing of the defects may occur with proper placement of the mesh in the mouth.

However, these methods also have certain drawbacks. Most specifically, if the mesh material is woven, its edges may become unravelled. In addition, at the point of attachment of the ligatures to the mesh, holes are created through which epithelial tissue could conceivably migrate. This is especially true if the holes are of unspecified dimension, so that there is no coordination between the ligature and the mesh. Also, such hole formation may itself result in a defect in the mesh integrity. In this manner, ineffective healing of the periodontal defect may result.

SUMMARY OF THE INVENTION

Therefore, it is an object of the present invention to provide a dental implant in which a ligature is attached to a bioabsorbable mesh material wherein a minimum number of attachment holes are created in the absorbable mesh.

It is a second object of the present invention to provide a dental implant wherein the essentially continuous edges of the dental implant are sealed and reinforced and present no possibility of unravelling.

It is yet another object of the present invention to provide a dental implant wherein the ligature material is formed from the same family of bioabsorbable materials as the bioabsorbable mesh used in the dental implant, and the ligature material fits into the attachment hole with an interference fit.

It is finally an object of the present invention to provide a bioabsorbable material which has ligature smoothly attached to it and contains sealed, reinforced edges to prevent unravelling of the mesh material.

These and other objects of the present invention are accomplished in a dental implant containing absorbable mesh material formed to fit on the surface of the tooth. This absorbable mesh construction contains all reinforced edges, which are fused as the result of laser cutting. In addition, the ligature attached to the mesh construction is formed from the same material as the mesh, and is attached so that there are no needle holes in the mesh and the ligature fits in an interference fit. The ligature may be attached by laser or ultrasonic welding or chemical resin typing or using an adhesive.

The invention will be better understood by reference to the accompanying drawings as well as the following detailed description of the invention wherein:

DETAILED DESCRIPTION OF THE INVENTION

During the procedure of the present invention, a diseased tooth is prepared by exposing the diseased portions of the tooth and periodontum. For example, the flaps of gingiva are reflected away from the tooth and surrounding bone. The defect can then be cleaned by periodontic techniques such as scaling, curetting or root planing.

At that point, a mesh insert construction 10 of the present invention is applied against the tooth surface 1 and extends toward the root at the level to which repair of the defect should occur.

The insert is formed from bioabsorbable polyesters of different constructions, but preferably the family of polyesters including VICRYL* (poly(L(-)lactide-coglycolide 10/90 M%). In older patients, where healing is slower, a polyester with slower bioabsorbable properties is preferable, such as PDS* (poly-p-dioxanone). In addition, other microdenier nonwoven fabrics are readily adaptable for use.

Figure 2:
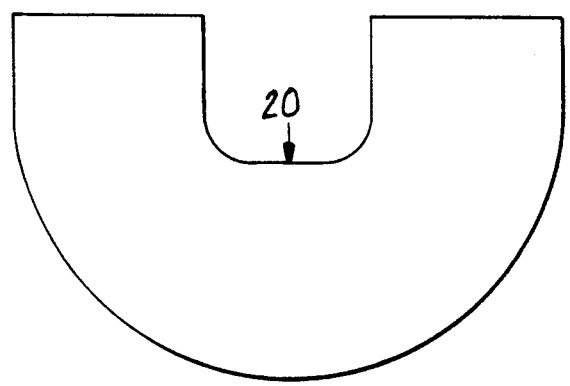
FIG. 2 is a plan view of an alternate combination of the present invention.
Figure 3:
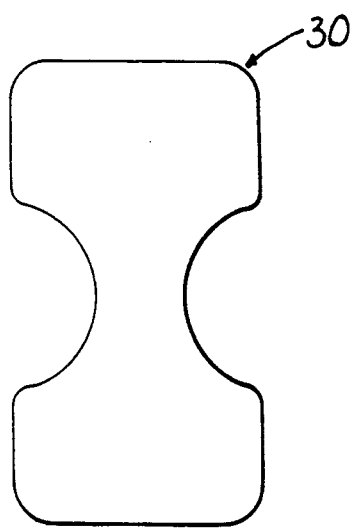
FIG. 3 is a plan view of another alternate combination of the present invention.

Alternate embodiments 20, 30 are seen in FIGS. 2 and 3. Both inserts 20, 30 fit snugly about the tooth, and have ligatures attached to them for this purpose. Inserts 20, 30 can be used especially well in instances such as delivery of medicine to a predetermined area of the tooth.

The patch or insert 10 is generally trapezoidal in shape. Its base width is about 13 mm, and it has a height of about 13 mm. It tapers to a width of about 9 mm. Preferably ligature attachments 14 are positioned at least 2 mm inside the edges of the patch 10. Ideally, the porous material insert 10 is placed to the level on the tooth just at the point where it is desired for the gingival epithelium to end.

Figure 4:
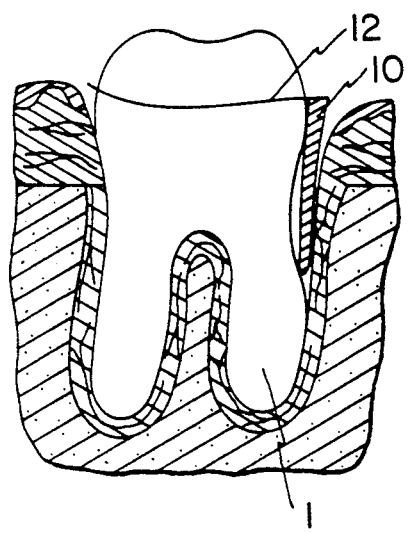
FIG. 4 is a view of a tooth with an implant of the present invention attached to the tooth.

As seen in FIG. 4, the insert 10 may then be wrapped around the perimeter of the tooth 1. It is placed at the portion of the perimeter where periodontal tissue attachment has been lost to disease. The patch 10 is placed against the tooth surface, and preferably extends from the tooth surface to cover any bony defects surrounding the tooth. The patch 10 also is secured directly under the gingiva so that it forms a protective barrier over the healing periodontal defect. The patch 10 should be closely attached to the tooth so that gingival epithelium cannot pass between the semiporous construction and the tooth surface.

The patch 10 may be tied around the tooth by the use of ligatures or filaments 12 attached to the patch 10. These ligatures 12 are used to hold the porous construction 12 snugly against the tooth. The ligature material in the present embodiment is made of the same bioabsorbable material as the patch 10, so that the ligature 12, too, is biocompatible and bioabsorbable within the body. Of course, it will be readily recognized that the materials used to make the patch 10 and ligature 12 need not be the same, as long as both are biocompatible and bioabsorbable.

Particularly important to this invention is the performance of laser cutting to create the patch 10. As can be appreciated, it is extremely important that the patch 10 not unravel and have smooth edges which will enhance the time of the patch 10 on the tooth surface 1. Also epithelial tissue attachment is avoided near these fused edges.

Because any bioabsorbable material must stay within the periodontal space for a period of time in order to allow healing of the periodontal defect, it is undesirable for the mesh to separate. This is especially true in a situation where the mesh is made from a woven material, which may have a tendency, when cut, to separate. Accordingly, in situations where a mesh patch is used, the mesh is cut using a laser cutting device, laser cutting creating localized heat enough to melt fibers but not enough to cause shrinkage, degradation or destruction of the patch 10. In this manner, the edge becomes welded, and is therefore not susceptible to separation. The patch then is able to be absorbed uniformly.

Once hydrolysis is effected, the periodontal ligament 12 begins to allow attachment of the alveolar bone to the tooth surface. The epithelium tissue has been prevented from moving apically along the periodontal defect, and proper attachment is made. In this manner, the tooth is therefore quite snugly bound within the mouth, and the sulcus is in an improved position at a higher point toward the crown.

Figure 1:
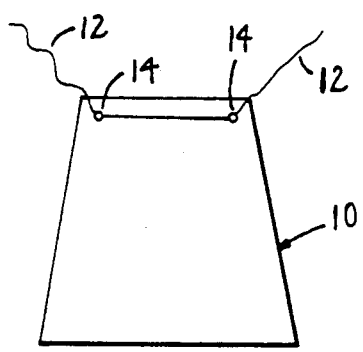
FIG. 1 is a plan view of a mesh (or similar nonwoven) construction and ligature combination of the present invention.

An additional aspect of the present invention is the attachment of the ligature material 12 to the patch 10. As can be seen in FIG. 1, the attachment must be effected without creating additional holes which may cause epithelial tissue leaks. In this case, the attachment is made by laser or ultrasonic assisted welding of ligature 12 to the semiporous mesh patch 10.

Alternately, the ligature 12 may be interwoven into the latticework of the mesh patch material 10. Similarly, there is no hole created in the mesh patch 10. Therefore, there will be no cell migration associated with growth of periodontal ligament or epithelial tissue during healing of the periodontal defect.

Such creation of a bioabsorbable mesh with the ligature attached in the foregoing manner produces various benefits. First, this allows tension during attachment to be placed on the ligature but not on the mesh material. In addition, as previously indicated, no holes are formed in the mesh. Because there are both fused edges and fused holes, there is no migration of epithelial cells through the holes onto the tooth surface.

Finally, because the semiporous mesh contains a smooth surface, it can be very easily used as a drug carrying means. In addition, ridge augmentation is possible. The patch can be filed with replacement or synthetic bone particles. The patch holds such particles in place until attachment to the alveolar bone occurs. Afterward, bioabsorption of the patch makes removal unnecessary. If the patch is also coated with medicament, various drugs can be simultaneously delivered to the oral cavity.

These and other objects of the present invention are to be understood from the following appended claims and their equivalents, which define the scope of the invention.

What is claimed is:

1. A dental implant comprised of bioabsorbable semiporous mesh material, said implant having sealed edges and emplaceable between the tooth and gingiva, wherein said implant is attached to the tooth by a bioabsorbable ligature material, said ligature material attached to said bioabsorbable mesh material, and wherein said mesh material holds bone particles in the interdental spaced in order to cause attachment of said particles to the tooth.

2. The implant of claim 1 wherein said implant is attached to the tooth by a ligature formed from a bioabsorbable material, said ligature material welded to said implant.

3. The implant of claim 2 wherein said material comprises polyl L(-) lactide co-glycolide.

4. The dental implant of claim 2 wherein said material comprises poly-p-dioxanone.

5. The implant of claim 1 wherein said ligature material is interwoven to said bioabsorbable mesh material.

6. A dental implant comprised of bioabsorbable semiporous mesh material, said implant having sealed edges and emplaceable between the tooth and gingiva, said edges sealed by ultrasonic welding, and said implant attached to the tooth by a bioabsorbable ligature material, said ligature material attached to said bioabsorbable mesh material, and wherein said mesh material holds bone particles in the interdental spaces in order to cause attachment of said particles to the tooth.

7. The implant of claim 6 wherein said ligature is welded to said implant.

8. The implant of claim 6 wherein said ligature material is interwoven to said bioabsorbable mesh material.

* * * * *